United States Patent [19]
Hileman et al.

[11] Patent Number: 5,441,051
[45] Date of Patent: Aug. 15, 1995

[54] METHOD AND APPARATUS FOR THE NON-INVASIVE DETECTION AND CLASSIFICATION OF EMBOLI

[76] Inventors: Ronald E. Hileman, 27 Redbud La., Lewistown, Pa. 17044; Brian Wall, 4414 Bleeker Ct., Raleigh, N.C. 27606; David A. Stump, 2565 Woodberry Dr., Winston-Salem, N.C. 27106

[21] Appl. No.: 386,297
[22] Filed: Feb. 9, 1995
[51] Int. Cl.⁶ .................................................. A61B 8/00
[52] U.S. Cl. ................................................ 128/661.08
[58] Field of Search ..................... 128/661.07, 661.08, 128/661.09, 661.10, 662.02, 662.04

[56] References Cited
U.S. PATENT DOCUMENTS
4,657,756 4/1987 Rasor et al. .................. 128/662.02

Primary Examiner—George Manuel
Attorney, Agent, or Firm—Rhodes, Coats & Bennett

[57] ABSTRACT

A method and apparatus for ultrasonically detecting an embolus in blood flow includes an ultrasound transducer for transmitting ultrasound pulses into the blood flow being interrogated and receiving reflections from acoustic impedance changes in the body. The reflected signals are converted to an electronic signal representation which is subsequently processed to detect and classify emboli in the blood flow. A short duration, broad bandwidth ultrasound signal is used to preserve the polarity of the reflected signal. The polarity is then used to classify the emboli based on a positive or negative reflection coefficient. Emboli having a negative reflection coefficient are classified as either gaseous or fat particles, and emboli having a positive reflection coefficient are classified as solid particles. The emboli can be further classified based on the amplitude of the reflected signal, or designated features of the time waveform or FFT of the reflected signal.

39 Claims, 3 Drawing Sheets

TIME

TIME

METHOD AND APPARATUS FOR THE NON-INVASIVE DETECTION AND CLASSIFICATION OF EMBOLI

FIELD OF THE INVENTION

The present invention relates generally to a method and apparatus for using ultrasound to detect emboli in the bloodstream, and more particularly, to an ultrasound detection apparatus for characterizing the emboli based on the size and composition of the embolic particles.

BACKGROUND OF THE INVENTION

It has long been known that strokes and other circulatory disorders can be the result of embolic particles carried by the bloodstream. More recently, it has become evident that large numbers of emboli occur during surgical procedures and that higher loss of neurological and physiological function is associated with higher numbers of emboli in the bloodstream supplying the brain. During surgery, clots may form in the blood, air may enter into the bloodstream, or tissue fragments may break loose or become dislodged. These emboli are carried by the blood into increasingly smaller arteries until they become lodged and obstruct the flow of blood. The mount of damage that results depends on the size of the emboli, the point in which it lodges in the blood flow, the amount of blood leaking around the emboli, and how blood is supplied by collateral paths around the obstruction. The resulting functional deficit depends in part on the composition of the emboli. For example, air may be reabsorbed in a short time, clots may dissolve (particularly if blood-thinning drugs are present), while particles composed of plaque and body tissue may not dissolve at all. Therefore, it is important to have non-invasive instrumentation that can determine the composition of emboli and estimate their size as well as count them so that appropriate medical management decisions can be made.

The present state of the art for non-invasive detection of emboli relies primarily on Doppler ultrasound to monitor blood vessels for the presence of emboli. When an emboli passes through an ultrasound beam, the change in acoustic reflectivity causes a strong reflection which can be detected by the ultrasound receiver. The number of embolic events can be counted by monitoring the amplitude of the Doppler signals. Embolic events are deemed to occur whenever the amplitude of the Doppler signal exceeds a predetermined threshold.

While the amplitude of the Doppler signal has been used effectively to detect and count emboli in the bloodstream, it does not provide sufficient information to characterize emboli based on composition and size. The amplitude of the Doppler signal may be affected by the size, composition, and/or shape of the emboli. The amplitude is also a function of transducer beam shape and of the location of the embolus relative to the sound beam. Because of these variables, the amplitude of the Doppler signal alone does not provide unambiguous information about the composition or size of the emboli. For example, the amplitude of the Doppler signal produced by a small ,gas bubble may be stronger than the signal from a large clot. In certain surgical procedures, the composition of the emboli (e.g., solid or gaseous) may be an important factor in determining the clinical procedures necessary to avoid complications arising from the presence of the emboli.

In the past, characterization of the emboli based on the time waveform of the Doppler signal has been attempted. However, the time waveform is highly variable with blood velocity, transducer beam shape, the position of the embolus within the ultrasound beam, and the composition of the embolus. For example, the amplitude of the time waveform may be effected by the position of the emboli within the sound beam (with emboli near the center of the beam producing larger amplitude signals than emboli near the edges of the beam) as well as the size and composition of the emboli. Similarly, the duration of the time waveform may be effected by the blood velocity, as well as the position of the emboli within the sound beam (with emboli near the ultrasound beam focus producing a shorter duration signal than emboli away from the focus). The interdependence of these variables makes it difficult to extract reliable information from the time waveform concerning the size and composition of the emboli.

Recently, attempts have been made to characterize emboli by using two or more ultrasound beams with varying frequencies to differentiate between gaseous and solid emboli. Such a system is described in U.S. Pat. No. 5,248,015 to Moehring, et al., and in an article entitled, *"Pulse Doppler Ultrasound Detection, Characterization and Size Estimation of Emboli in Flowing Blood"* published in *Transactions on Biomedical Engineering*, Vol. 41, No. 1, January, 1994. This method uses the ratio of the acoustic power backscattered from the embolus to that of the moving blood surrounding the embolus. This ratio is called the "embolus-to-blood ratio" (EBR). It is postulated that the ratio of EBR at two different frequencies will be one value for solid emboli within certain operational limits, and that the ratio of EBR at the same two different frequencies for gas emboli will be another value. Thus, emboli can be characterized by comparing the ratio of the EBR of the reflected signals at two or more different frequencies.

While the characterization of emboli based on the "embolus-to-blood ratio" of multiple signals is promising it has several drawbacks. First, this method requires measurements at two or more frequencies which increases the complexity of the system. Secondly, this method may have difficulty with emboli that resonate. The resonance of the emboli will vary with size and may alter the amplitude ratio at different Doppler frequencies.

It has long been known that the reflection coefficient of particles will vary based on the composition of the particles. This natural phenomenon is true for emboli as well as other types of materials. For emboli that are less dense that blood (i.e., gas and fat particles), the reflection coefficient is negative. The reflection coefficient will be positive for emboli which are more dense than blood (such as clots and plaque). A negative reflection coefficient means that the phase of the reflected signal will be inverted 180 degrees from that of the incident signal. If the phase of the incident signal is known, then it is possible to compare it with the phase of the reflected signal to determine if the unknown embolus is of higher or lower impedance than blood.

With a pulse Doppler or continuous wave Doppler signal, it is difficult to determine the absolute phase of the reflected signal because of the nature of Doppler detection. The Doppler detection system looks at the change of phase with time to measure the frequency shift but does not utilize absolute phase. In order to determine absolute phase, the phase of the incident wave must be known very precisely at the range of the embolus. Thus, the range of the embolus from the transducer must be known within a small fraction of an acoustic wavelength.

It is not possible for continuous wave Doppler to measure range. Pulse Doppler can measure range but not with sufficient accuracy since pulse Doppler systems are typically narrow bandwidth, often in the 20 percent to 30 percent range. This means that the received echo signal will build up gradually over several cycles of the carrier frequency so it is very difficult to determine precisely when it starts. While the signal is relatively large after several cycles, it is necessary to project this phase back to the precise beginning of the pulse with an accuracy of better than one-quarter of a cycle. Since current Doppler systems do not have this range resolution accuracy, they have not been able to use the phase of the reflected signal and have had to revert to less direct methods to predict the impedance of the emboli.

SUMMARY AND OBJECTS OF THE INVENTION

The present invention relates to a method and apparatus for ultrasonically detecting emboli in blood flow, and for characterizing such emboli by composition and size. A short duration, broad bandwidth ultrasound pulse is used to insonify the blood flow being interrogated. Reflections from the acoustic impedance changes in the body return to the transducer which converts the reflected signal back into an electrical signal. In order to preserve the polarity of the reflected signals, a short duration, broad bandwidth signal is used. The percent bandwidth of the ultrasound signal is preferably in excess of 50% and more preferably about 80%, and its duration is preferably less than one cycle of the center frequency of the ultrasound signal. The reflected signals from the body are then converted to an electronic signal representation and are analyzed to detect the presence of emboli in the blood flow, and to characterize such emboli. A moving target indicator is used to eliminate reflections from the vessel walls and surrounding tissue. When an emboli passes through the ultrasound beam, the change in acoustic reflectivity causes a strong reflection which can be detected by the ultrasound receiver. The number of embolic events is counted by monitoring the amplitude of the signals. Embolic events are deemed to occur whenever the amplitude of the signal exceeds a predetermined threshold.

When an emboli is detected, the signal is analyzed to determine its polarity to separate gaseous and fat particles from more dense, solid emboli. Emboli, such as gas and fat particles, which are less dense than blood, will have a negative polarity. Solid emboli, which are more dense than blood, will have a positive polarity. Further classification of the emboli using a combination of well-known techniques may also be employed. The amplitude of the signals can be analyzed to provide information concerning the size of the embolus. The time waveform and/or frequency spectrum of the echo returned from the embolus may also be useful in classifying the embolus.

DETAILED DESCRIPTION OF THE INVENTION

Figure 1:
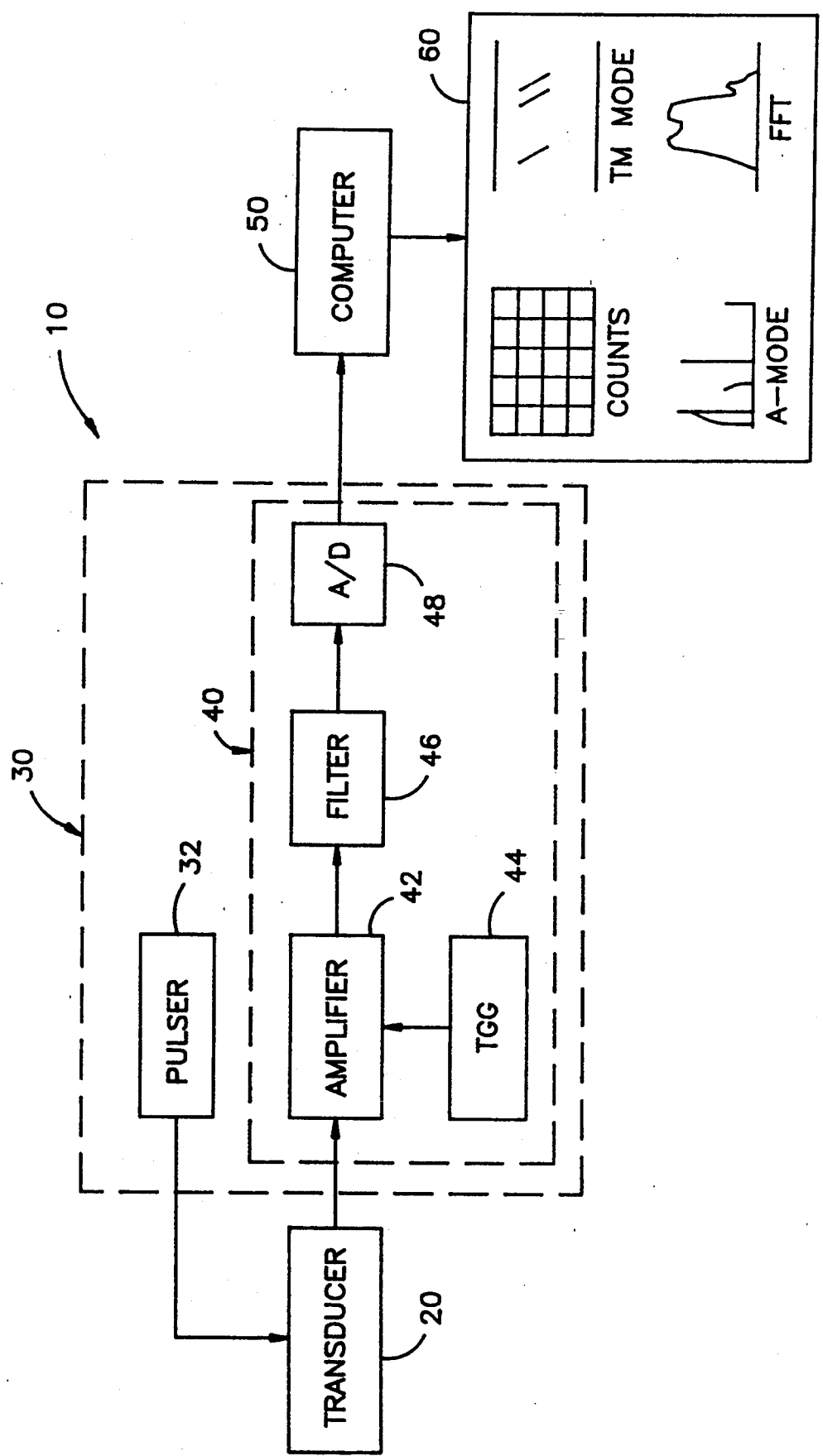
FIG. 1 is a block diagram of the ultrasound detection system of the present invention.

Referring now to the drawings, in particularly to FIG. 1, there is shown an emboli detection apparatus which is indicated by the numeral 10. The emboli detection apparatus includes an ultrasound transducer 20, a transducer interface 30 including a receiver 40, a general purpose programmable computer 50, and a conventional CRT display 60.

The ultrasound transducer 20 is used to both transmit ultrasound pulses into the body and receive echoes or reflections from within the body. The transducer 20 is preferably a PZT composite and has a quarter wave impedance matching layer to increase the coupling of sound from the transducer 22 into the patient's body. A pulser 32, which is part of the transducer interface 30, applies fast-rise time step pulses to the transducer 20 which is converted by the transducer 20 into ultrasound signals that reflect off the blood flow being interrogated. Typically, the drive pulse is over 100 volts and rise times are on the order of 15 nanoseconds.

Reflections from the acoustic impedance changes in the body return to the transducer 20 which converts the reflected acoustic energy back into an electronic signal. It is important that the transducer 20 has a broad bandwidth so it can preserve the polarity of the reflected signals. It is preferred that the percent bandwidth of the ultrasound signal be at least 50%, and more preferably at least 80%. For example, an ultrasound signal having a range between 3 MHz and 7 MHz will have a center frequency of 5 MHz and a percent bandwidth of 80%. The duration of the signal is preferably less than one cycle of the center frequency of the ultrasound signal. If the ultrasound signal is centered at 5 MHz, then the duration of the pulse should be less than approximately 200 nanoseconds. For purposes of this application, the duration of the signal is considered to be the length of time the signal remains above one-half the maximum amplitude of the signal. The ultrasound beam should be broad and unfocused so as to cover the entire cross section of the artery being interrogated. A plurality of ultrasound transducers 20 may be arranged in an array and operated sequentially to produce adjacent beams that collectively cover the entire cross-section of the blood vessel.

The ultrasound beam is preferably angled with respect to the blood flow direction so that the effective range from the transducer face to the embolus changes as the embolus passes through the sound beam. This change in the range with respect to time produces the well-known moving target indicator (MTI) shift. A good choice of angle is 60 degrees between the axis of the sound beam and the axis of the blood vessel. Angling the beam serves two useful functions. First, it makes the moving target shift much larger than that of the surrounding tissue so that the moving target indicator (described below) has a much easier task of separating the reflections from surrounding tissue. Secondly, an angled beam reduces the strength of specular reflections from the vessel walls so that the dynamic range requirements for detection' and signal processing are reduced.

The transducer interface 30 also includes a receiver 40 which amplifies the small electrical output from the transducer 20 to a level suitable for analyzing and processing. The receiver 40 includes an amplifier 42, a time gain compensation (TGC) circuit 44, a filtering circuit 46, and an analog-to-digital converter 48. The amplifier 42 amplifies the signal from the transducer 20 to a level suitable for processing. The TGC circuit 44 applies a signal to the amplifier 42 that causes its gain to increase with time to compensate for the acoustic attenuation experienced as the ultrasound pulse travels deeper into the body. The filter circuit 46 employs a band pass filter to reduce the out-of-band noise and artifact signals while preserving time and frequency characteristics of the reflected signals. The receiver 40 preferably has a low frequency cut-off that is around one-fourth the center frequency of the transducer 20 so that the echo pulses are not differentiated and made into bi-polar pulses that are harder to classify.

The receiver 40 also includes an analog-to-digital (AD) converter 48 that converts the signal to digital form for subsequent processing. Analog-to-digital conversions need to take place at a rate high enough to preserve the characteristics of the reflected signal from the embolus. With an ultrasound signal centered at 5 MHz, analog-to-digital conversions rates should be 20 MHz or higher. The AD converter 48 must also have sufficient accuracy to preserve amplitude and polarity information. A ten or twelve bit AD converter 48 will typically have sufficient accuracy for practicing the present invention.

The output of the AD converter 48 is passed to a general purpose digital computer 50 for subsequent processing. The electronic signal representations of the echo pulses are stored in the computer memory. Approximately 250 to 500 samples are typically stored for each transmit/receive sequence. The signals are processed by software running on the digital purpose digital computer. The computer 50 analyzes the electronic signal representations of the echo pulses and uses the results to classify the emboli based on size and composition. The results of the emboli detection and classification can be shown on a conventional CRT display 60 connected to the general purpose digital computer 50. Also the computer 50 may produce an audible tone in response to the detection of the emboli.

Figure 2:
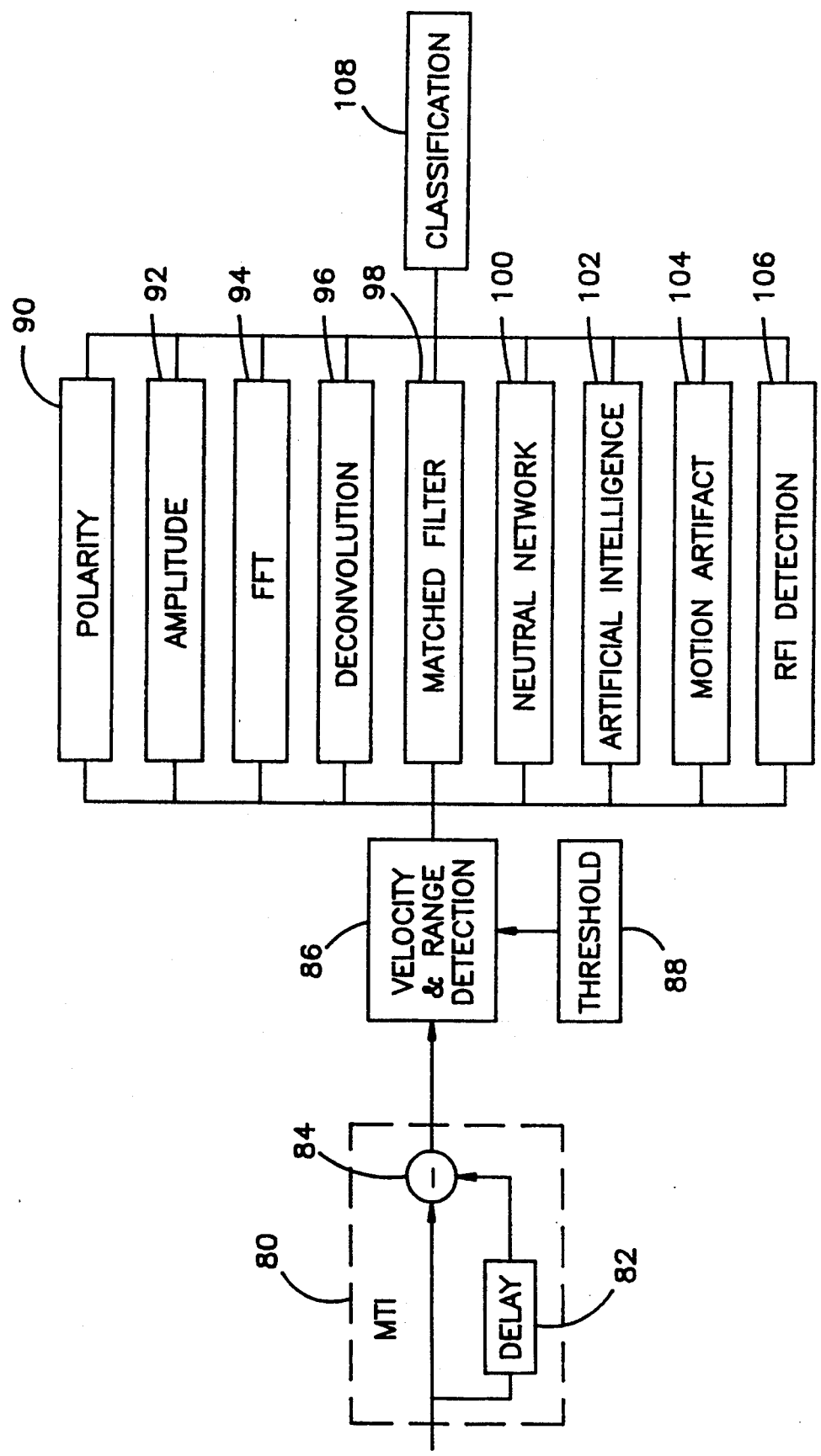
FIG. 2 is a block diagram illustrating the signal processing steps for detecting and characterizing emboli in the blood flow.

Referring now to FIG. 2, a block diagram of the various signal processing steps involved in the detection and classification of emboli is shown. The first step in the processing of the signal is to separate the signals representative of reflections from the flowing blood (which includes reflections of emboli contained in the blood flow) from reflection's off of the vessel walls and surrounding tissue within the sound beam. The reflections from surrounding tissue are generally stronger than those from the flowing blood and from the emboli. The strong reflections from surrounding tissue may be reduced using a moving target indicator (MTI) represented generally by the numeral 80. In order to factor out the signals reflected from surrounding body tissue, one line of echo data is stored in a temporary storage area 82 and is subtracted from a subsequent line of echo data as indicated at 84. By obtaining the difference between two lines of echo data, the signals from reflections off surrounding body tissue are largely canceled leaving the signal reflected from the blood flow and the emboli contained therein.

The simple moving target indicator (MTI) described above can be improved in several well-known ways. The noise performance can be improved by averaging multiple lines so that the signal-to-noise ratio is improved and obtaining the difference between the averages. The signal-to-noise ratio improves by a factor of the square root of the number of lines averaged when the noise is incoherent and the signal is coherent. A reasonable number of lines to average is sixteen. The averaging of multiple lines will result in a waveform that responds slowly to changes. Therefore, it will not change significantly even when an embolus passes through the ultrasound beam. The subtraction will, however, show a large difference when an embolus is present in the ultrasound beam.

In order to detect emboli at different velocities and different ranges, the present invention employs multiple velocity and range detection bins 86. The emboli are carried along by the blood flow and generally move at the same velocity as the blood. Blood flow velocity, however, is not constant during the heart cycle. The blood flow increases during systole and decreases during diastole. Blood flow is also faster in the center of the vessel than along the walls due to wall friction. In the preferred embodiment, multiple velocity detection channels are employed, each channel matched to a different range of velocities. Therefore, the channel having the highest magnitude output will indicate approximately how fast the embolus is moving.

Similarly, multiple range detection bins are used to cover all ranges across the blood vessel. A high speed digital computer can compute the signal levels falling in each range bin and detect those signals exceeding a predetermined threshold. Separate signal processing channels are provided for all velocities at each range so that both the range and velocity of the embolus will be known when a signal meeting the threshold criteria is detected. This allows the subsequent analyzing and processing steps to be focused on a narrow region in the velocity and range by excluding all other velocities and ranges. Since emboli should generally be occurring a relatively low rates, more computationally intensive methods can be used.

The threshold criteria 88 can be set manually by the user or it can be adjusted by automatically. The purpose of the threshold is to prevent false-positive counts by rejecting noise without missing embolic events. The automatic threshold can be set based on the power of the ultrasound signal reflected from the moving blood.

Once the embolus signal is detected, it is then analyzed to classify the emboli. The present invention initially classifies emboli based on the polarity of the reflected signal as indicated at 90. Additionally, the present invention relies on other methods for classification including amplitude 92, the Fast Fourier Transform (FFT) 94, deconvolution 96, matched filters 98, neural networks 100, and artificial intelligence 102.

The polarity of the first strong reflection from the embolus is used to separate gaseous and fat particles from dense, solid emboli. For emboli such as gas and fat particles which are less dense than blood, the reflection coefficient will be negative. The reflection coefficient will be positive for more dense material such as clots and plaque. A negative reflection coefficient means that the phase of the reflected signal will be inverted 180 degrees from that of the incident signal. Thus, by determining the polarity of the signal, it is possible to determine whether the acoustic impedance of the embolus is higher or lower than blood.

Figure 3A:
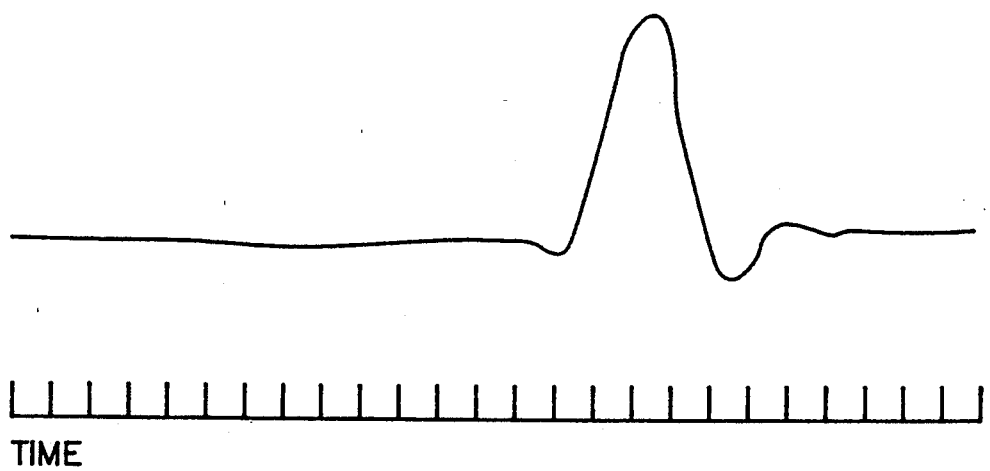
FIGS. 3($a$) and 3($b$) are typical time waveforms produced by reflections from emboli in the blood flow.
Figure 3B:
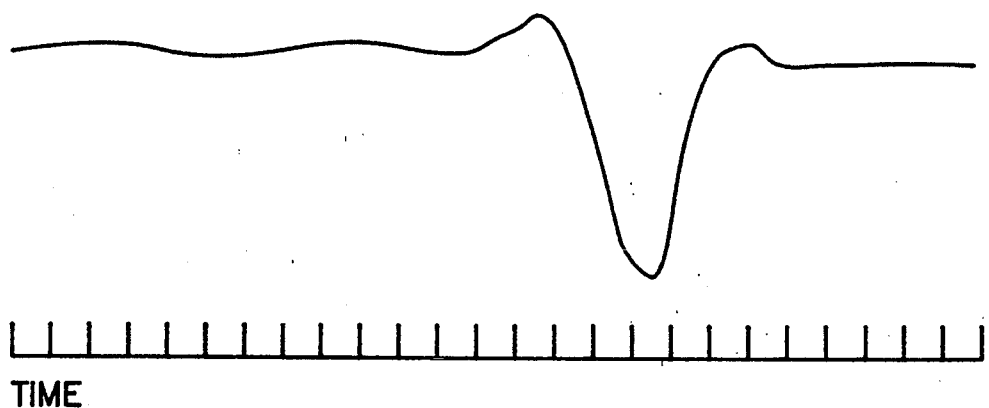

Referring now to FIGS. 3(A) and 3(B), two echo pulses of opposite polarity and varying arrival times are shown. Because the present invention employs a short duration, broad bandwidth signal, it is possible to easily determine the polarity of the signals without the need to determine the range of the embolus. This is not possible with current Doppler systems because they lack the range resolution accuracy necessary to determine, the polarity of the reflected signal. The signal shown in FIG. 3(A) is characteristic of an emboli composed of clotted blood or plaque which would have a positive reflection coefficient. The signal shown in FIG. 3(B) is characteristic of an emboli such as gas or fat particles having a negative reflection coefficient. The polarity information is used to separate gaseous from solid emboli.

Further classification of the emboli using a combination of well-known techniques may also be employed. The amplitude of the signals can be analyzed to provide information concerning the size of the embolus. Discrete Fourier Transform (DFT) or Fast Fourier Transform (FFT) can be applied to the time waveform to obtain a frequency spectrum of the signals. Suitable analyzing and processing techniques include deconvolution, matched filters, neural networks and artificial intelligence techniques. These techniques are described in probability, random, variables and stochastic processes by Athanasios Papelis published by McGraw-Hill in 1965, *Introduction to Expert Systems,* 2nd Edition by Peter Jackson, published by Addison Wesley Publications in 1990; and *Artificial Network Systems, Foundations, Paradigm, Application and Implementation* by Patrick K. Simpson, published by Pergamen Press in 1990. These references are incorporated herein by reference. The frequency spectrum can be analyzed and processed using the same techniques applied to the time waveform. The analysis and processing methods can be implemented using a high-speed digital computer.

The digital computer may also be used to detect motion artifacts and radio frequency interference (RFI). Movements of the patient and/or transducer will cause large outputs from the moving target indicator. To separate motion artifacts from true embolic events, the computer uses a motion artifact detection 104 function to inhibit counting during periods when abnormal movement is detected at most ranges and velocities. True embolic signals will not be detected during this abnormal condition but since emboli are a rare occurrence and since movement artifacts should be of short duration, this is probably not a serious concern.

Interference signals from other equipment in the operating room may also interfere with the desired signals. The preferred embodiment employs an RFI detection function 106 to recognize these abnormal conditions on the basis of strong signals being present at most ranges and most velocities. Counting is inhibited when interference conditions are present.

Once the signal is analyzed using the techniques described above, the embolic events are classified and counted as indicated at 108. The polarity feature can be used to separate emboli into gaseous and solid classes. All major classes of emboli can be broken down on the basis of echo signal amplitude. For particles smaller than an acoustic wavelength, the reflected pulse time waveform will be very similar to the transmitted pulse. The amplitude will be proportional to the size of the particle. This means that gaseous particles can be further classified by size based on amplitude after the initial classification based on a negative reflection coefficient. Similarly, particles initially classified as solid on the basis of having positive reflection coefficients may be subclassified by size based on amplitude.

The major classes of emboli can be further subdivided on the basis of differing time patterns or frequency patterns. Soft particles whose size is larger than an acoustic wavelength are likely to transmit a substantial portion of the incident sound through the particle and will produce a second reflection from the back surface. This reflection will have the opposite polarity of the first surface. The presence of two relatively equal amplitude echoes of opposite polarity closely following each other suggest an embolus composed of soft material. The time spacing between the echoes is proportional to the size of the particle.

Hard particles equal to or larger than a wavelength may produce multiple internal reverberations. The ting-down time may be used to deduce the size and elastic properties of the particle.

Larger gas bubbles may produce acoustic waves that travel around the surface of the bubble producing multiple decaying echoes. The resonance frequency of this surface wave depends on the size of the bubble.

The frequency spectrum of the emboli may also provide information concerning the composition of the embolus. The center frequency of the spectrum will vary with the acoustic nature of the embolus. The spectrum may be smooth or have sharp dips. The presence and spacing of the dips may correspond to the presence and time separation of the front and back reflections from the emboli. The depth of the dips may provide information on the absorption properties of the emboli.

The examples given above illustrate some of the ways for classifying emboli. The echo patterns observed to date from different embolic particles have many subtle variations in the time waveform and in the corresponding frequency spectrums. The classification of the emboli based on these factors can be implemented using a decision tree structure on a digital computer.

The results of the emboli classification function can be shown on a display 60. The format of the display may take a variety of forms. The display may show a table with the numbers of emboli of different sizes for each major type. It can show a visual representation of the echo signal. For example, a time motion display (TM) of the raw signal from the moving target indicator can be displayed. The amplitude of the time waveform versus time (A-mode) can be displayed. It can also show a frequency spectrum of the FFT waveform.

Based on the foregoing, it is apparent that the present invention provides an improved method for detecting and classifying emboli in the bloodstream. The present invention employs a short duration, broad bandwidth pulse which can be easily analyzed to determine the polarity or phase of the reflected signal. The polarity of the reflected signal could be used to classify emboli into gaseous and solid classes. Once the emboli is initially classified on the basis of polarity, then conventional techniques can be used to further classify the emboli without the ambiguities in hand in conventional Doppler detection systems. That is, once an initial classification of the emboli is made on the basis of polarity, then further classification based on the amplitude of the signal, the time waveform or the FFT of the signal can be made more reliably.

What is claimed is:

1. An ultrasonic pulse echo apparatus for detecting an embolus in blood flow, comprising:
    a) at least on ultrasound transducer for transmitting short duration, broad bandwidth ultrasound pulses through a blood vessel so that emboli passing through the vessel are insonified;
    b) an ultrasound receiver for receiving echo pulses from an emboli passing through said blood vessel and from surrounding tissue and for converting said echo pulses into an electronic signal representation; and
    c) signal processing means for processing said electronic signal representation of said echo pulses to detect the presence of an emboli and to characterize said emboli by determining the polarity of the electronic signal representation of the echo pulses.

2. The pulse echo system of claim 1 wherein said ultrasound transducer has a percent bandwidth greater than 50%.

3. The pulse echo system of claim 2 wherein said ultrasound transducer has a percent bandwidth greater than 80%.

4. The pulse echo system of claim 1 wherein the ultrasound beam covers the entire cross-section of the blood vessel.

5. The pulse echo system of claim 4 including a plurality of ultrasound transducers arranged in an array and operated to sequentially produce adjacent beams that collectively cover the entire cross-section of the blood vessel.

6. The pulse echo system of claim 1 wherein the ultrasound receiver has a frequency response extending below one-fourth the nominal center frequency of the ultrasound transducer to facilitate preservation of the polarity of said echo pulses.

7. The pulse echo system of claim 1 wherein the ultrasound receiver includes time gain compensation to compensate for acoustic attenuation of said ultrasound pulses.

8. The pulse echo system of claim 1 wherein said signal processing means includes a moving target indicator to differentiate echo pulses of said emboli from echo pulses of the surrounding tissue.

9. The pulse echo system of claim 8 wherein said moving target indicator includes a smoothing function for averaging multiple pulse echo sequences.

10. The pulse echo system of claim 1 wherein said signal processing means further characterizes said emboli by size based on the amplitude of said electronic signal representation.

11. The pulse echo system of claim 1 wherein said signal processing means generates a time waveform based on said electronic signal representation of the echo pulses and further characterizes said emboli based upon selected features of said time waveform.

12. The pulse echo system of claim 1 wherein said signal processing means generates a frequency spectrum based on said electronic signal representation of said echo pulses and further characterizes said emboli based upon selected features of said frequency spectrum.

13. The pulse echo system of claim 1 wherein said signal processing means maintains a count of the number of emboli having certain designated characteristics.

14. The pulse echo system of claim 1 wherein said signal processing means includes means to detect motion artifacts.

15. The pulse echo system of claim 14 wherein said signal processing means inhibits detection of emboli when motion artifacts are present.

16. The pulse echo system of claim 1 wherein said signal processing means includes means for detecting electrical interference artifacts.

17. The pulse echo system of claim 16 wherein said signal processing means inhibits detection of emboli when electrical interference artifacts are present.

18. The pulse echo system of claim 1 further including means for classifying said emboli based upon selected features of said electronic signal representation of the echo pulses from said emboli.

19. The pulse echo system of claim 1 further including a display for providing a visual representation of the echo pulses from the emboli.

20. The pulse echo system of claim 19 wherein the visual representation of the echo pulse is an amplitude versus time display.

21. The pulse echo system of claim 19 wherein the visual representation of the echo pulse is an amplitude versus frequency display.

22. The pulse echo system of claim 19 wherein the visual representation of th echo pulse is time versus depth display wherein amplitude is represented as brightness.

23. The pulse echo system of claim 1 further includes means for generating an audible signal in response to the detection of an emboli.

24. A method for ultrasonically detecting an embolus in blood flow comprising:
    (a) transmitting a short duration, broad bandwidth ultrasound pulse through a blood vessel so that emboli passing through the vessel are insonified;
    (b) receiving echo pulses from the emboli passing through the blood vessel and from surrounding tissue at a receiver;
    (c) converting the echo pulses into an electronic signal representation;
    (d) processing said electronic signal representation of said echo pulses to detect the presence of an emboli; and
    (e) characterizing said emboli by determining the polarity of the electronic signal representation of the echo pulses.

25. The detection method of claim 24 wherein the ultrasound pulses transmitted through the blood vessel have a percent bandwidth greater than 50%.

26. The detection method of claim 25 wherein the ultrasound pulses transmitted through the blood vessel have a percent bandwidth greater than 80%.

27. The detection method of claim 24 wherein the ultrasound beam covers the entire cross-section of the blood vessel.

28. The detection method of claim 27 wherein an array of ultrasound pulses are transmitted sequentially, and wherein said array of ultrasound pulses collectively cover the entire cross-section of the blood vessel.

29. The detection method of claim 24 further including the step of detecting abnormal motion and inhibiting detection of emboli when abnormal motion is present.

30. The detection method of claim 24 further including the step of detecting electrical interference and inhibiting detection of emboli when electrical interference is present.

31. The detection and classification method of claim 24 further including the step of characterizing said emboli by size based on the amplitude of said electronic signal representation.

32. The detection and classification method of claim 24 further including the step of generating a time waveform based on said electronic signal representation of the echo pulses and characterizing said emboli based upon selected features of said time waveform.

33. The detection and classification method of claim 24 further including the step of generating a frequency spectrum on said electronic signal representation of said echo pulses and characterizing said emboli based upon said features of said frequency spectrum.

34. The detection and classification method of claim 24 further including the step of maintaining a count of the number of emboli having certain designated characteristics.

35. The detection and classification method of claim 24 further including the step of displaying a visual representation of the echo pulses from the emboli.

36. The detection and classification method of claim 35 wherein the visual representation of the echo pulse is an amplitude versus time display.

37. The detection and classification method of claim 35 wherein the visual representation of the echo pulse is an amplitude versus frequency display.

38. The pulse echo system of claim 35 wherein the visual representation of the echo pulse is a time versus depth display wherein amplitude is represented as darkness.

39. The pulse echo system of claim 24 further including the step of generating an audible signal in response to the detection of an emboli.

* * * * *